United States Patent [19]
Wurster

[11] Patent Number: 5,376,960
[45] Date of Patent: Dec. 27, 1994

[54] VIDEO ENDOSCOPE WITH SOLID-STATE IMAGING DEVICE

[75] Inventor: Helmut Wurster, Oberderdingen, Germany

[73] Assignee: Richard Wolf GmbH, Knittlingen, Germany

[21] Appl. No.: 943,347

[22] Filed: Sep. 10, 1992

[30] Foreign Application Priority Data

Sep. 10, 1991 [DE] Germany .............. 4129961

[51] Int. Cl.⁵ .................................. H04N 5/247
[52] U.S. Cl. .................................... 348/76
[58] Field of Search .......... 358/98, 229; 128/6; 348/65, 76; H04N 5/247

[56] References Cited

U.S. PATENT DOCUMENTS

| | | | |
|---|---|---|---|
| 4,646,721 | 3/1987 | Arakawa | 128/6 |
| 4,745,470 | 5/1988 | Yabe et al. | 358/98 |
| 4,745,471 | 5/1988 | Takamura et al. | 358/98 |
| 4,757,805 | 7/1988 | Yabe | 128/6 |
| 4,779,130 | 10/1988 | Yabe | 358/98 |
| 4,786,965 | 11/1988 | Yabe | 358/98 |
| 4,809,680 | 3/1989 | Yabe | 128/6 |
| 4,831,456 | 5/1989 | Takamura | 358/98 |
| 4,832,003 | 5/1989 | Yabe | 128/6 |
| 4,867,138 | 9/1989 | Kubota et al. | 358/98 |
| 4,890,159 | 12/1989 | Ogiu | 358/98 |
| 4,918,521 | 4/1990 | Yabe et al. | 358/98 |
| 4,971,035 | 11/1990 | Ito | 358/98 |
| 4,993,405 | 2/1991 | Takamura et al. | 358/98 |

FOREIGN PATENT DOCUMENTS 4015633 11/1990 Germany .

Primary Examiner—Tommy P. Chin
Assistant Examiner—Richard Lee
Attorney, Agent, or Firm—Panitch Schwarze Jacobs & Nadel

[57] ABSTRACT

A video endoscope has in its distal end region an objective lens, a semi-conductor imager assigned to it and further electronic components provided for wiring it. In order to further reduce the required diameter of the endoscope shaft compared to the known designs, the electronic components are arranged on an integral ceramic substrate, on which the conductors for joining and for connecting these parts are directly placed.

6 Claims, 4 Drawing Sheets

VIDEO ENDOSCOPE WITH SOLID-STATE IMAGING DEVICE

BACKGROUND OF THE INVENTION

1. Field of the Invention

The invention relates to a video endoscope, in the distal end region of which an objective lens, a semi-conductor imager assigned to it and further electronic components are arranged. Video endoscopes of this type are suitable for investigating body cavities and for carrying out any operations there at the same time.

2. Description of the Prior Art

Video endoscopes of the type mentioned in the introduction are used in various designs. Hence, U.S. Pat. No. 4,918,521 shows such a instrument, in which the semi-conductor imager includes a solid-state imaging chip, in front of which an optical lens system is placed and which is arranged essentially at right angles to a circuit substrate, so that a spatial arrangement of solid-state imaging chip, substrate and electronic components is made possible. These parts are thus shaped by casting to form an endoscope tip which can be incorporated into an endoscope or even into a camera housing, This specification shows a series of embodiments which differ essentially in the arrangement and mutual assignment of the said elements. The common feature here is that the individual components are applied and wired on the circuit substrate provided with connections. The disadvantage here is that the individual hybrids are relatively large and their wiring is difficult and therefore complex.

A video endoscope can also be seen from U.S. Pat. No. 4,809,680 which combines the above-mentioned components in the endoscope tip, but wherein it is designed as a pre-assembled insert, into which the optical system and the electronic components arranged on it can be inserted and which can be attached to the end of a flexible endoscope shaft.

Reference may also be made to U.S. Pat. No. 4,745,470, U.S. Pat. No. 4,832,003 and U.S. Pat. No. 4,757,805, from which endoscope tips of similar design can also be seen.

The constructions disclosed in the cited specifications all have one or more plate bars for the CCD chip and the other electronics as well as a mounting connected therewith for the optical system. These elements are then cast to form an endoscope head. Only after completing this casting process does the endoscope head achieve its full stability, wherein the disadvantages known from the state of the art according to U.S. Pat. No. 4,918,521 also exist in these designs.

It is the object of the invention to indicate a construction for the distal end region of a generic video endoscope which makes it possible to further reduce the diameter compared to the known solutions; at the same time a simpler construction for the video endoscope head should be achieved.

SUMMARY OF THE INVENTION

This object is achieved according to the invention in that the objective lens, the semi-conductor imager and further electronic components are arranged on an integral ceramic substrate, to which the conductors for joining and for connecting the electronic components and the semi-conductor imager are directly attached, and which sits within the endoscope shaft and is supported by it.

The advantages which can be achieved using this design consist particularly in that, in addition to using the advantages of the ceramic materials known per se—reference may be made, for example to the favourable temperature properties—direct application of the electronic components, primarily of the CCD chip, makes it possible to save on the mostly ceramic substrate platelets for the individual components. Furthermore, the otherwise conventional bases may be dispensed with, and additional space is gained because of the lack of the connecting lugs of the electronic components which claim a relatively large amount of space, so that the diameter of the video endoscope may be reduced or more space is available for accommodating the other components, optical system, light guides, instrument channels, intake channels and rinsing channels, electronics and electrical connections.

According to a preferred embodiment, the ceramic substrate may have an essentially cuboid support part, the width of which is smaller than the internal diameter of the endoscope shaft and to which a disc-shaped centering part is connected on the end-face side, which extends essentially vertically to the longitudinal extension of the support part and its external contour is adapted to the internal contour of the endoscope shaft.

A ceramic substrate designed in this manner offers relatively large surfaces for the arrangement of said parts with a very low space requirement. It is thus advantageous if the centering part is provided with bores, for example for receiving light guides, for introducing an auxiliary instrument, for supplying rinsing liquid and for attaching electrical connections, since this makes complete and exact pre-assembly of the video endoscope head possible without further aligning and mounting aids. In order to thus align the flexible light guides precisely with respect to the optical system, it is possible to have the objective lens mounted on a ceramic platelet which can be attached to the support part and has bores provided for receiving light guides, which bores are arranged to be aligned with those in the centering part.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

DESCRIPTION OF THE PREFERRED EMBODIMENTS

Figure 1:
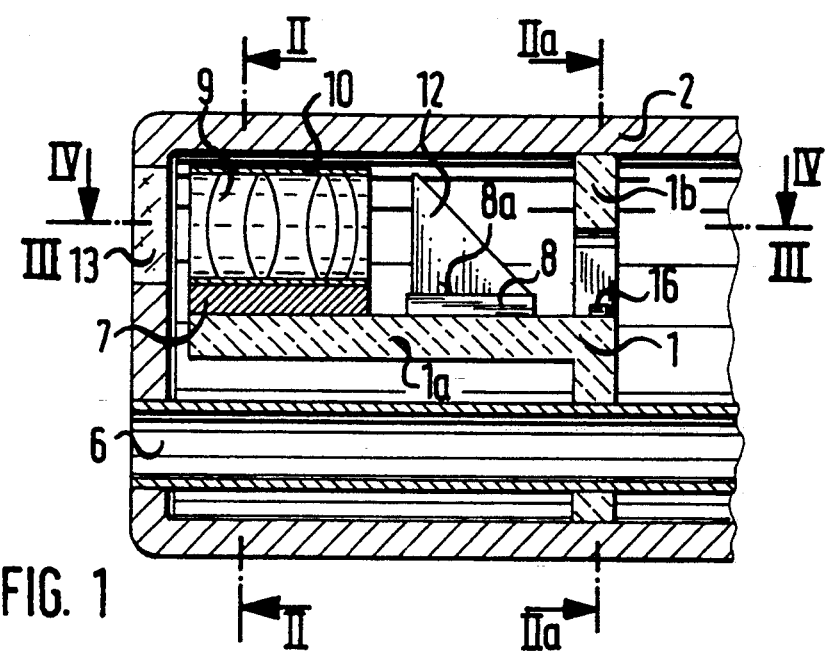
FIG. 1 shows a longitudinal section through a video endoscope head according to the invention.
Figure 2:
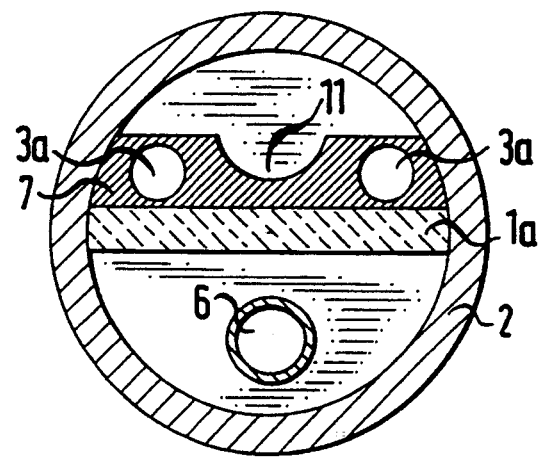
FIG. 2 shows a section along the section line II—II in FIG. 1.
Figure 2A:
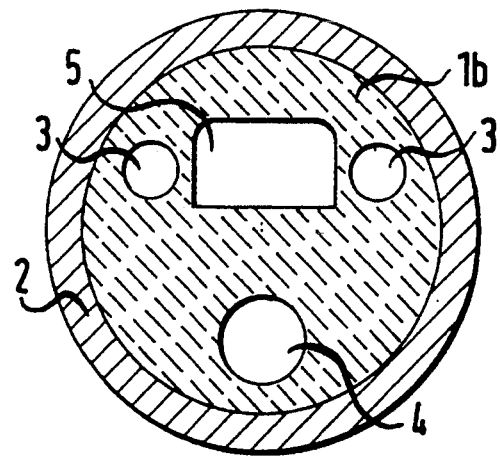
FIG. 2a shows a section along the section line IIa—IIa in FIG. 1.
Figure 3:
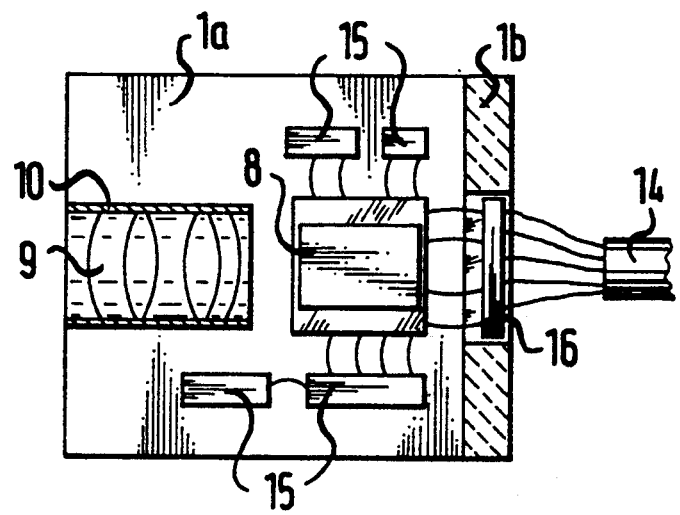
FIG. 3 shows a section along the line III—III in FIG. 1.

The following description relates initially to the embodiment according to FIGS. 1, 2, 2a and 3, which show the distal endoscope head of a video endoscope. As can be seen, this head comprises a substrate 1 which is made from a ceramic material. The ceramic substrate 1 has the shape of a T. A part extending in the direction of the endoscope axis is designed as support part 1a and has the shape of a cuboid. A centering part 1b, which is adapted to the internal contour of the cylindrical endoscope shaft 2, is connected to the support part 1a at right angles. The centering part 1b is provided with bores 3 and 4 as well as a opening 5, as can be seen in FIG. 2a. An auxiliary instrument channel 6 is passed through the bore 4. The bores 3 serve to introduce the light guides through the centering part 1b. The opening 5 is required for attaching electrical connections.

As can also be seen from FIGS. 1 and 2, a platelet 7 preferably made from the same ceramic material as the substrate 1 and a solid-state imaging chip (CCD) 8 are arranged on the top side of the support part 1a. The platelet 7 serves as support part for some of the optical elements which are surrounded by a metal cylinder 10 and form the endoscope objective lens 9. The metal cylinder 10 is attached in a recess 11 in the platelet 7. The platelet 7 also has bores 3a which are aligned with the bores 3 in the centering part 1b and serve to introduce the light guides. In this exemplary embodiment, a prism 12 is arranged above the solid-state imaging chip 8 and serves to divert the image taken up by the objective lens 9 onto the solid-state imaging chip 8 arranged with its image surface 8a in a plane parallel to the longitudinal axis of the endoscope in this example. The end of the endoscope is finally sealed in conventional manner with a light-permeable cover platelet 13 in the region of the objective lens 9.

Figure 4:
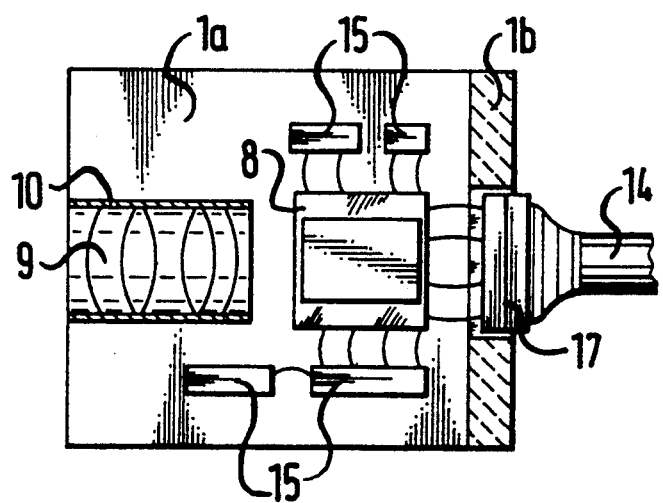
FIG. 4 shows an alternative embodiment to that represented according to FIG. 3 with a plug board for the connection of signal lines and electronics.

Electronic components 15, which are attached directly to the ceramic of the support part 1a complete with the solid-state imaging chip 8 itself, serve to wire the solid-state imaging chip 8. The electrical connection of the attached electronic components 8 or 15 to one another is carried out in known manner, for example by bonding or by vapour-deposited strip conductors or similar measures. The connection between the electronics situated on the support part 1a and the signal lines 14 leading in the proximal direction is made by means of a tag block 16 according to FIG. 3, while this task is taken over by a plug board 17 in the embodiment according to FIG. 4.

Figure 5:
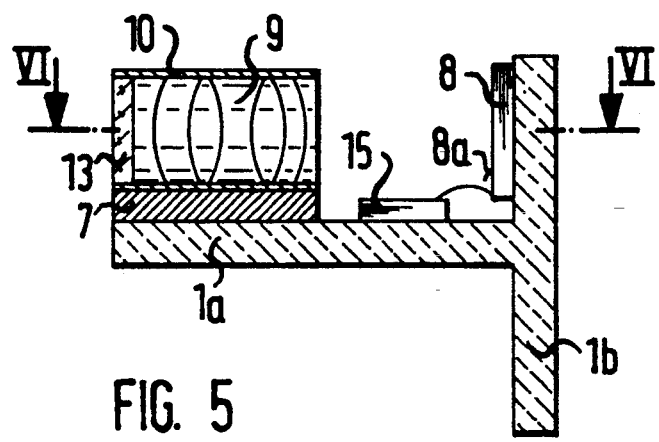
FIG. 5 shows a modified design of the video endoscope head in longitudinal section.
Figure 6:
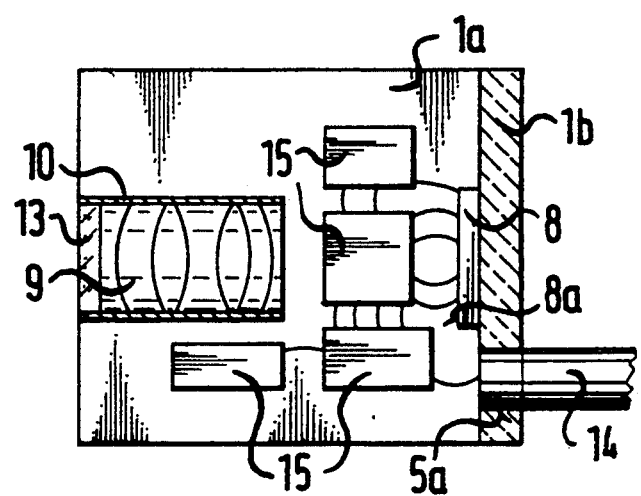
FIG. 6 shows a longitudinal section through the representation according to FIG. 5 along the section line VI—VI.

In the embodiment of the distal endoscope head according to the invention shown in FIGS. 5 and 6, a likewise essentially T-shaped substrate 1 is used, on which the endoscope objective lens 9 and the electronic components 15 are arranged for wiring the solid-state imaging chip 8. These components are attached in the same way as described above. However, the difference with respect to the example according to FIGS. 1 to 4 consists in that the solid-state imaging chip 8 is arranged vertically to the optical axis of the objective lens 9 with its imaging surface 8a pointing in the direction of the objective lens. The ceramic substrate 1 is therefore also modified here to the effect that the opening for contact between electronics and signal lines 14 is arranged not as in FIG. 2a, but as lateral opening 5a, as can be seen in FIG. 6. The bores 3 for the light guides are of course also attached in a modified manner, but this is not shown. As in the case of the previous exemplary embodiment, in the example according to FIGS. 5 and 6, the electronic components are also attached directly to the ceramic support 1 in the manner already outlined and, as also described above, connected to one another electrically. The connection between electronics and signal lines takes place in the lateral opening 5a, in particular again either by means of a tag block or plug board.

Figure 7:
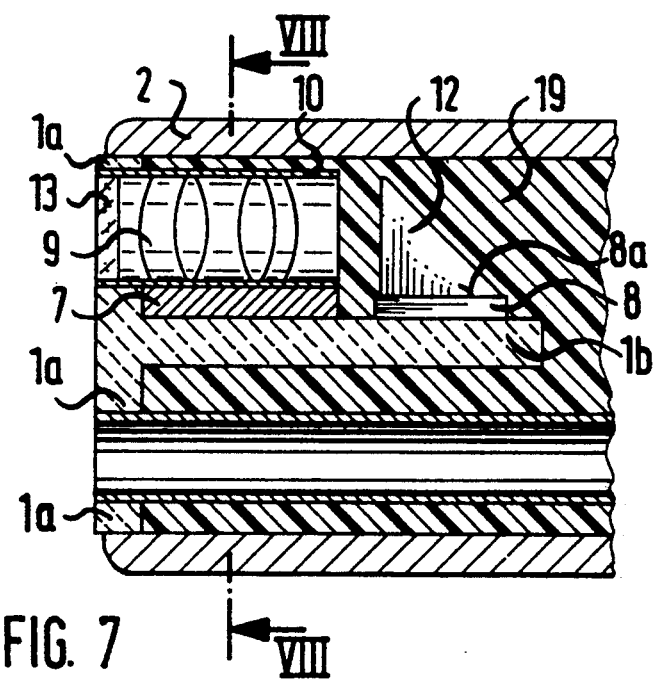
FIG. 7 shows a further variant of a video endoscope head in longitudinal section.
Figure 8:
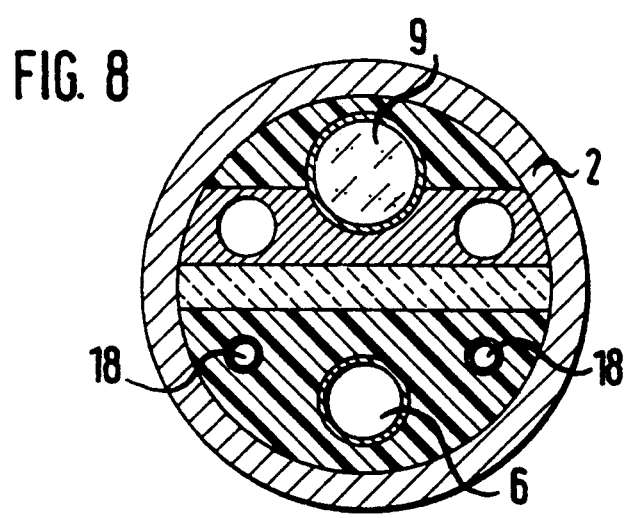
FIG. 8 shows a section along the section line VIII—VIII in FIG. 7.

In the embodiment of the distal endoscope head shown in FIGS. 7 and 8, a ceramic substrate 1 of essentially T-shaped design is again used, but wherein the centering part 1a aligned vertically to the endoscope axis forms the distal end of the endoscope and the cuboid support part 1b points proximally in the direction of the endoscope axis. The arrangement of the endoscope objective lens 9 and the electronic components 8 or 15 takes place here in the manner previously described for the embodiment according to FIGS. 1 to 4. As can be seen from FIG. 8, two rinsing channels 18, by means of which the light-permeable cover platelet 13 in front of the distal end of the objective lens 9 can be rinsed free of impurities, are provided in addition to the channels already mentioned, so that an optimum image can always be achieved.

All components, but at least the electronic components, are advantageously fixed by casting by means of a light-permeable plastic 19, as indicated for all exemplary embodiments applicable to FIG. 7.

The present invention may be embodied in other specific forms without departing from the spirit or essential attributes thereof and, accordingly, reference should be made to the appended claims rather than to the foregoing specification as indicating the scope of the invention.

I claim:

1. A video endoscope comprising an objective lens, a semiconductor imager assigned to the objective lens, electronic components, conductors for joining and connecting the electronic components to the semiconductor imager, and a ceramic substrate arranged inside and directly supported by a distal end region of an endoscope shaft of the video endoscope, said ceramic substrate being constructed as a common carrier for the objective lens, the imager and the electronic components, said ceramic substrate comprising a generally cuboid-shaped support part having a width smaller than an internal diameter of the endoscope shaft, the ceramic substrate also comprising a generally disc-shaped centering part having an end-face side connected to the support part, the centering part extending essentially vertically to a longitudinal extension of the support part and having an external contour essentially corresponding to and fixed to an internal contour of the endoscope shaft.

2. A video endoscope according to claim 1 wherein said centering part has bores for at least one of the following: receiving light guides, introducing an auxiliary instrument, supplying rinsing liquid, and attaching electrical connections in the video endoscope.

3. A video endoscope according to claim 1 wherein the objective lens is mounted on a ceramic platelet, the ceramic platelet being attached to the support part and having bores for receiving light guides.

4. A video endoscope comprising an objective lens, a semiconductor imager assigned to the objective lens, electronic components, conductors for joining and connecting the electronic components to the semiconductor imager, and a ceramic substrate arranged inside and directly supported by a distal end region of an endoscope shaft of the video endoscope, said ceramic substrate being constructed as a common carrier for the objective lens, the imager and the electronic components, the ceramic substrate comprising a centering part having bores for at least one of the following: receiving light guide, introducing an auxiliary instrument, supplying rinsing liquid, and attaching electrical connections in the video endoscope.

5. A video endoscope according to claim 4 wherein the ceramic substrate also comprises a support part coupled with the centering part, and wherein the objective lens is mounted on a ceramic platelet, the ceramic platelet being attached to the support part and having bores aligned with the centering part bores for receiving light guides.

6. A video endoscope comprising an objective lens, a semiconductor imager assigned to the objective lens, electronic components, conductors for joining and connecting the electronic components to the semiconductor imager, and a ceramic substrate arranged inside and directly supported by a distal end region of an endoscope shaft of the video endoscope, said ceramic substrate being constructed as a common carrier for the objective lens, the imager and the electronic components, and the objective lens being mounted on a ceramic platelet, the ceramic platelet being attached to the substrate and having bores for receiving light guides.

* * * * *